United States Patent
Aziz et al.

(10) Patent No.: US 7,169,482 B2
(45) Date of Patent: Jan. 30, 2007

(54) DISPLAY DEVICE WITH ANTHRACENE AND TRIAZINE DERIVATIVES

(75) Inventors: Hany Aziz, Burlington (CA); Nan-Xing Hu, Oakville (CA); Zoran D. Popovic, Mississauga (CA); Ah-Mee Hor, Mississauga (CA)

(73) Assignee: LG.Philips LCD Co., Ltd., Seoul (KR)

( * ) Notice: Subject to any disclaimer, the term of this patent is extended or adjusted under 35 U.S.C. 154(b) by 0 days.

(21) Appl. No.: 10/372,547

(22) Filed: Feb. 24, 2003

(65) Prior Publication Data

US 2004/0018383 A1    Jan. 29, 2004

Related U.S. Application Data

(63) Continuation-in-part of application No. 10/207,686, filed on Jul. 26, 2002, now abandoned.

(51) Int. Cl.
*H01L 51/50* (2006.01)
*H05B 33/14* (2006.01)

(52) U.S. Cl. .............. 428/690; 428/917; 313/504; 313/506; 257/102

(58) Field of Classification Search .......... 428/690, 428/917; 313/504, 506; 257/102
See application file for complete search history.

(56) References Cited

U.S. PATENT DOCUMENTS

| 5,935,721 A | 8/1999 | Shi et al. ............. 428/690 |
| 5,972,247 A | 10/1999 | Shi et al. ............. 252/583 |
| 6,057,048 A | 5/2000 | Hu et al. ............. 428/690 |
| 6,225,467 B1 | 5/2001 | Esteghamatian et al. .... 544/180 |
| 6,229,012 B1 | 5/2001 | Hu et al. ............. 544/180 |
| 6,465,115 B2 * | 10/2002 | Shi et al. ............. 428/690 |
| 2002/0004146 A1 * | 1/2002 | Kido et al. ............. 428/690 |

FOREIGN PATENT DOCUMENTS

| EP | 1 009 044 | 6/2000 |
| EP | 1 009 044 A2 | 6/2000 |
| EP | 1221473 A1 * | 7/2002 |

OTHER PUBLICATIONS

Proceedings of SPIE—The International Society for Optical Engineering, 4105 (Organic Light-Emitting Materials and Devices (IV), p. 251-255, (2001).*
Copy of Communication from European Patent Office.

* cited by examiner

*Primary Examiner*—Dawn L. Garrett
(74) *Attorney, Agent, or Firm*—McKenna Long & Aldridge LLP (57) ABSTRACT

A device includes:
an anode;
a cathode; and
a luminescent region between the cathode and the anode, wherein the luminescent region includes an anthracene derivative compound and a triazine derivative compound.

17 Claims, 2 Drawing Sheets

DISPLAY DEVICE WITH ANTHRACENE AND TRIAZINE DERIVATIVES

CROSS REFERENCE TO RELATED APPLICATIONS

This application is a continuation-in-part application of parent U.S. application Ser. No. 10/207,686 (filed Jul. 26, 2002) (now abandoned), from which priority is claimed, the disclosure of which is totally incorporated herein by reference.

BACKGROUND OF THE INVENTION

Organic light emitting devices ("OLEDs") represent a promising display technology. To realize a full color display, OLEDs emitting in the red, green, and blue regions of the visible spectrum are needed. Recent advances led to the development of green and red emitting OLEDs of satisfactory performance. However, there is still a need, which the present invention addresses, to improve the performance of blue emitting OLEDs, more specifically to increase their operational stability and to enhance color purity.

The following documents may be relevant to the present application:

Hu et al., U.S. Pat. No. 6,229,012 B1
Esteghamatian et al., U.S. Pat. No. 6,225,467 B1
Hu et al., U.S. Pat. No. 6,057,048
Shi et al., U.S. Pat. No. 5,935,721
Shi et al., U.S. Pat. No. 5,972,247
Shi et al., EP 1 009 044 A2.

SUMMARY OF THE INVENTION

The present invention is accomplished in embodiments by providing a device comprising:
an anode;
a cathode; and
a luminescent region between the cathode and the anode, wherein the luminescent region comprises an anthracene derivative compound and a triazine derivative compound.

In other embodiments, there is provided a device comprising:
an anode;
a cathode; and
a luminescent region between the cathode and the anode, wherein the luminescent region comprises an anthracene derivative compound and a triazine derivative compound, wherein the anthracene derivative compound is selected from the group consisting of formulas I(A)(1) through I(A)(11), formula I(B), formula I(C), and formula I(D), and the triazine derivative compound is selected from the group consisting of formulas II(A), II(B), II(C), and II(D) wherein the formulas and substituents are discussed herein.

BRIEF DESCRIPTION OF THE DRAWINGS

Other aspects of the present invention will become apparent as the following description proceeds and upon reference to the Figures which represent preferred embodiments.

Unless otherwise noted, the same reference numeral in different Figures refers to the same or similar feature.

DETAILED DESCRIPTION

The following guidelines are provided:

(1) The term "layer" indicates a single coating generally having a composition that differs from the composition of an adjacent layer.

(2) The term "region" refers to a single layer, a plurality of layers such as two, three or more layers, and/or one or more "zones."

(3) The term "zone," as used in the context of the charge transport zone (i.e., hole transport zone and electron transport zone) and the light emitting zone, refers to a single layer, a plurality of layers, a single functional area in a layer, or a plurality of functional areas in a layer.

(4) The phrase anthracene derivative compound refers to a family of related unsubstituted and substituted compounds that all contain the same structural unit of three fused benzene rings as represented by following structural formula

I where illustrative examples of the anthracene derivative compound are provided herein.

(5) The phrase triazine derivative compound refers to a family of related unsubstituted and substituted compounds that all contain the same structural unit of an aromatic heterocycle in which any three of the CH atoms of benzene are replaced by nitrogen atoms in a consecutive or non-consecutive manner such as at the 1,2,3 positions, at the 1,2,4 positions, at the 1,2,5 positions, at the 1,2,6 positions, or at the 1,3,5 positions. Replacement by the nitrogen atoms may be at for example the 1,3,5 positions, as represented by the following structural formula

II where illustrative examples of the triazine derivative compound are provided herein.

(6) In embodiments where a layer containing the anthracene derivative compound and/or the triazine derivative compound could be equally viewed as being functionally or physically part of an electrode or other non-luminescent region, the convention here is that such a layer containing the anthracene derivative compound and/or the triazine derivative compound is considered part of the luminescent region.

(7) The phrase "a non-anthracene and non-triazine derivative compound" refers to a compound other than an anthracene derivative compound and a triazine derivative compound.

The present organic light emitting device ("OLED") includes within the luminescent region at least one anthracene derivative compound and at least one triazine derivative compound. Any suitable layer sequence and layer composition may be employed to accomplish the present invention.

Figure 1:
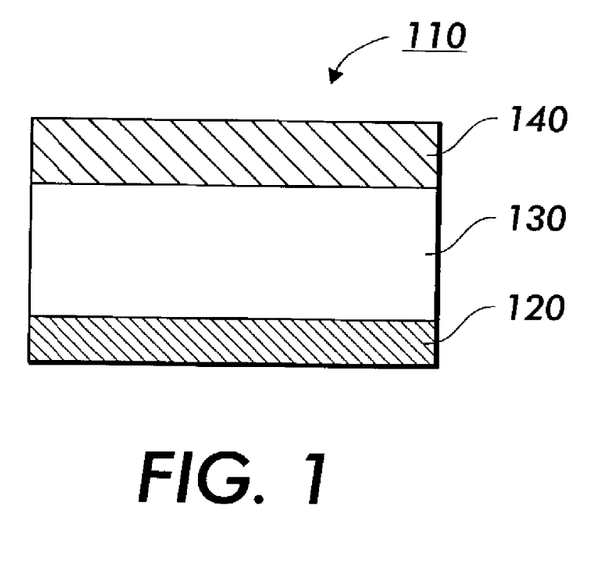
FIG. 1 illustrates a schematic, elevational view of a first embodiment of the present invention.

A first exemplary embodiment is seen in FIG. 1 where the OLED 110 is composed of in the depicted sequence: an anode 120; a luminescent region 130; and a cathode 140.

Figure 2:
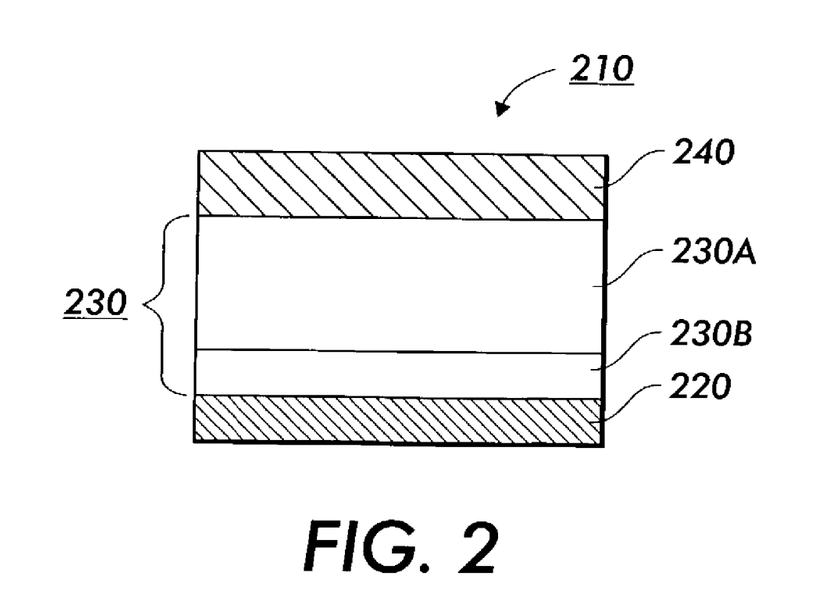
FIG. 2 illustrates a schematic, elevational view of a second embodiment of the present invention.

A second exemplary embodiment is seen in FIG. 2 where the OLED 210 is composed of in the depicted sequence: a first electrode 220; a luminescent region 230 composed of a light emitting zone 230B and a charge transport zone 230A; and a second electrode 240. The first electrode can be the cathode while the second electrode is the anode; alternatively, the first electrode can be the anode while the second electrode is the cathode. The charge transport zone can be a hole transport zone when the second electrode is the anode; alternatively, the charge transport zone can be an electron transport zone when the second electrode is the cathode.

Figure 3:
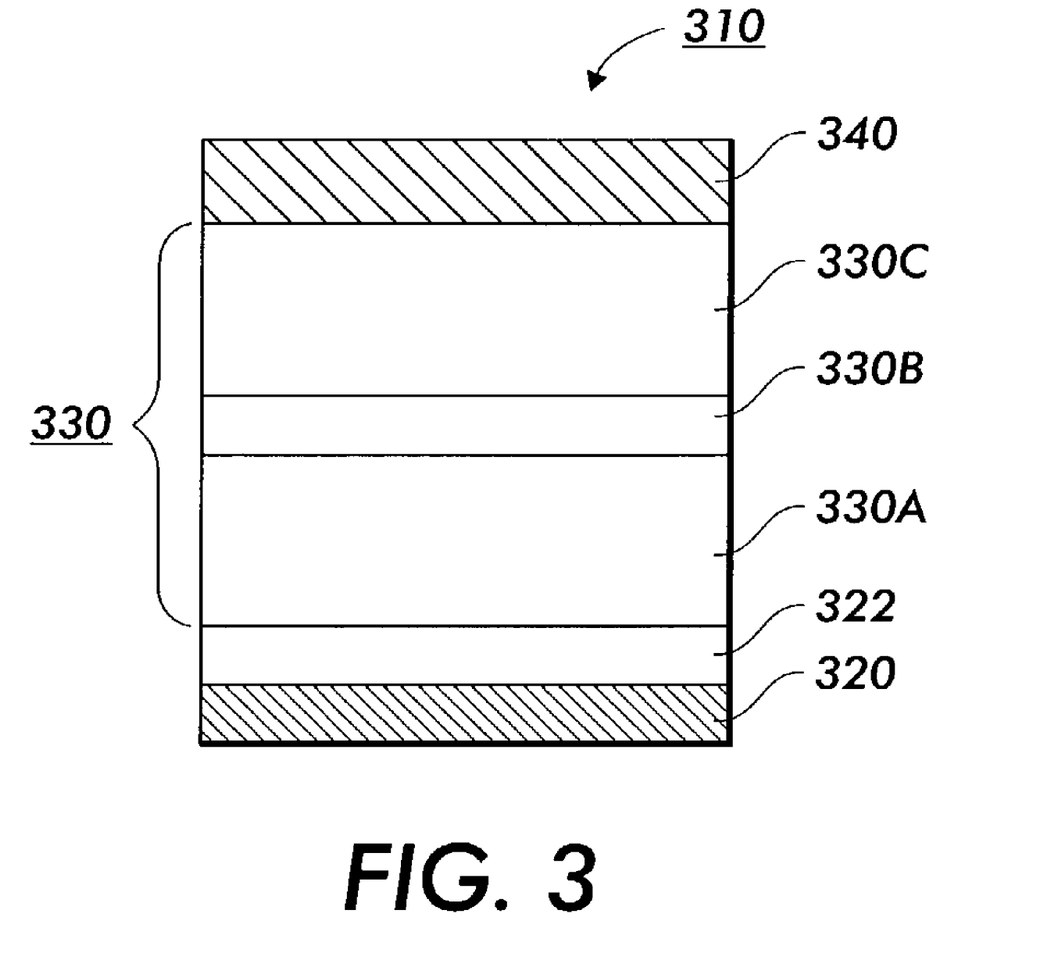
FIG. 3 illustrates a schematic, elevational view of a third embodiment of the present invention.

A third exemplary embodiment is seen in FIG. 3 where the OLED 310 is composed of in the depicted sequence: an anode 320; an optional buffer layer 322; a luminescent region 330 composed of a hole transport zone 330A, a light emitting zone 330B, and an electron transport zone 330C; and a cathode 340.

For convenience, a substrate is not depicted in FIGS. 1–3; it is understood however that a substrate may be positioned at any suitable place in the depicted OLEDs such as in contact with either electrode.

The at least one triazine derivative compound may be present as one, two, three or more compounds. Where two or more triazine derivative compounds are present, they may be in a mixture of equal or unequal ratios; or the triazine derivative compounds may be in an unmixed state such as separately disposed in different layers or in different areas of a single layer. In embodiments, the at least one triazine derivative compound may be considered an electron transport material because the transport of electrons is greater than the transport of holes through the triazine derivative compound. In embodiments, a number of the triazine derivative compounds, in addition to being electron transporters, may also be a blue emitter, i.e., a material wherein holes and electrons can combine to result in the emission of light in the blue region of the visible spectrum.

The at least one anthracene derivative compound may be present as one, two, three or more compounds. Where two or more anthracene derivative compounds are present, they may be in a mixture of equal or unequal ratios; or the anthracene derivative compounds may be in an unmixed state such as separately disposed in different layers or in different areas of a single layer. In embodiments, the at least one anthracene derivative compound is a type of an organic electroluminescent material that may be considered a blue emitter, i.e., a material wherein holes and electrons can combine to result in the emission of light in the blue region of the visible spectrum. In embodiments, a number of the anthracene derivative compounds may also be able to transport holes, electrons, or both holes and electrons at a poor, fair, good, or excellent level. Since in embodiments the anthracene derivative compounds may be both a blue emitter and a charge conductor, this dual property allows a degree of flexibility in placement of the anthracene derivative compounds in the OLEDs.

The at least one anthracene derivative compound and the at least one triazine derivative compound may be present in one, two or more layers, zones, or regions of the instant OLEDs such as the following exemplary OLED configurations (where two or more anthracene derivative compounds are present in the OLED, such anthracene derivative compounds may be the same or different from one another; and where two or more triazine derivative compounds are present in the OLED, such triazine derivative compounds may be the same or different from one another):

(1) anode/light emitting zone (anthracene derivative compound)/electron transport zone (triazine derivative compound)/cathode.

(2) anode/light emitting zone (anthracene derivative compound+triazine derivative compound)/electron transport zone (non-anthracene and non-triazine derivative compound)/cathode.

(3) anode/light emitting zone (anthracene derivative compound+triazine derivative compound)/electron transport zone (triazine derivative compound)/cathode.

(4) anode/light emitting zone (anthracene derivative compound+triazine derivative compound)/electron transport zone (anthracene derivative compound+triazine derivative compound)/cathode.

(5) anode/light emitting zone (anthracene derivative compound)/electron transport zone (anthracene derivative compound+triazine derivative compound)/cathode.

(6) anode/light emitting zone (anthracene derivative compound)/electron transport zone (a first layer of anthracene derivative compound+triazine derivative compound, and a second layer of a triazine derivative compound)/cathode.

(7) anode/light emitting zone (anthracene derivative compound)/electron transport zone (a first layer of anthracene derivative compound+triazine derivative compound, and a second layer of non-anthracene and non-triazine derivative compound)/cathode.

(8) anode/hole transport zone (anthracene derivative compound)/light emitting zone (anthracene derivative compound+triazine derivative compound)/electron transport zone (triazine derivative compound)/cathode.

(9) anode/hole transport zone (anthracene derivative compound)/light emitting zone (anthracene derivative compound+triazine derivative compound)/electron transport zone (non-anthracene and non-triazine derivative compound)/cathode.

(10) anode/hole transport zone (anthracene derivative compound)/light emitting zone (anthracene derivative compound+triazine derivative compound)/cathode.

(11) anode/hole transport zone (anthracene derivative compound)/light emitting zone (triazine derivative compound)/cathode.

(12) anode/hole transport zone (anthracene derivative compound)/light emitting zone (triazine derivative compound)/electron transport zone (triazine derivative compound)/cathode.

(13) anode/hole transport zone (anthracene derivative compound)/light emitting zone (triazine derivative compound) /electron transport zone (non-anthracene and non-triazine derivative compound)/cathode.

(14) anode/hole transport zone (anthracene derivative compound)/light emitting zone (non-anthracene and non-triazine derivative compound)/electron transport zone (triazine derivative compound)/cathode.

In exemplary configurations 6,7 the layer of anthracene derivative compound+triazine derivative compound can be equally viewed as being part of the light emitting zone.

In exemplary configurations 1 through 7, the configurations can optionally further include a hole transport zone (adjacent the anode) which may comprise an anthracene derivative compound and/or a non-anthracene and non-triazine derivative compound.

In exemplary configurations 8 through 14, the configurations can optionally further include in the hole transport zone (adjacent the anode) a non-anthracene and non-triazine derivative compound.

The luminescent region including the anthracene derivative compound and the triazine derivative compound can be one, two, three or more layers. For example, for a single layer luminescent region, the anthracene derivative compound and the triazine derivative compound can be deposited with varying concentrations across the thickness of the layer such that two functional areas are produced: a light emitting zone (e.g., anthracene derivative compound+triazine derivative compound) and an electron transport zone (e.g., anthracene derivative compound+triazine derivative compound), where the concentration of the anthracene derivative compound in the electron transport zone is for example less than that in the light emitting zone, or, optionally, even completely absent from the electron transport zone. In embodiments, there is provided a single layer luminescent composed of a mixture of an anthracene derivative compound and a triazine derivative compound, with a constant concentration throughout. A multi-layer luminescent region can be composed for example of the following: a light emitting layer in contact with a charge transport layer; and a light emitting layer between a hole transport layer and an electron transport layer.

The light emitting zone can include a single anthracene derivative compound, or a mixture of two or more anthracene derivative compounds. Where a mixture of two or more anthracene derivative compounds are used, the anthracene derivative compounds may be present in any suitable ratio by weight such as equal or unequal amounts; one compound in the mixture may be present for instance in an amount ranging from 0.1% to 99.9% by weight, the balance being the other compound(s). In addition to the anthracene derivative compound(s), a charge transport material may be present in the light emitting zone at a concentration ranging for example from 0% to about 95% by weight based on the light emitting zone, the balance being the anthracene derivative compound(s) at a concentration ranging from 100% to about 5% by weight based on the light emitting zone.

Alternatively, the light emitting zone can include a single triazine derivative compound, or a mixture of two or more triazine derivative compounds. Where a mixture of two or more triazine derivative compounds are used, the triazine derivative compounds may be present in any suitable ratio by weight such as equal or unequal amounts; one compound in the mixture may be present for instance in an amount ranging from 0.1% to 99.9% by weight, the balance being the other compound(s). In addition to the triazine derivative compound(s), a charge transport material may be present in the light emitting zone at a concentration ranging for example from 0% to about 95% by weight based on the light emitting zone, the balance being the triazine derivative compound(s) at a concentration ranging from 100% to about 5% by weight based on the light emitting zone.

Also, alternatively, the light emitting zone can include a mixture of anthracene derivative compound(s) and triazine derivative compound(s). Where a mixture of two or more of the anthracene derivative compound(s) and the triazine derivative compound(s) are used, each of the anthracene derivative compound(s) and the triazine derivative compound(s) may be present in any suitable ratio by weight such as equal or unequal amounts; one compound in the mixture may be present for instance in an amount ranging from 0.1% to 99.9% by weight, the balance being the other compound(s). In addition to the anthracene derivative compound(s) and the triazine derivative compound(s), a charge transport material may be present in the light emitting zone at a concentration ranging for example from 0% to about 95% by weight based on the light emitting zone, the balance being the anthracene derivative compound(s) and the triazine derivative compound(s) at a concentration ranging from 100% to about 5% by weight based on the light emitting zone.

In embodiments, the light emitting zone can include one or more non-anthracene and non-triazine derivative compounds in any suitable ratio by weight such as equal or unequal amounts. These one or more non-anthracene and non-triazine derivative compounds may be added to the light emitting zone to affect the color intensity or color purity of the emitted light as compared to a light emitting zone without such one or more non-anthracene and non-triazine derivative compounds. In embodiments of the present invention, blue emitting OLEDs are produced; in other embodiments, OLEDs emitting another color may be produced by the use of appropriate materials in the luminescent region such as by adding one or more non-anthracene and non-triazine derivative compounds to the light emitting zone to change the blue color to another color.

The charge transport zone (whether a hole transport zone or an electron transport zone) includes a single charge transport material or a mixture of two or more charge transport materials at any suitable ratio by weight such as equal or unequal amounts; one compound in the mixture may be present for instance in an amount ranging from 0.1% to 99.9% by weight, the balance being the other compound(s). The charge transport zone can include one or more anthracene derivative compound(s), one or more triazine derivative compound(s), one or more non-anthracene and non-triazine compound(s), or any mixture thereof.

The layers of the OLED may be transparent or opaque depending on the side of the OLED that is facing the viewer. Illustrative materials will now be discussed in constructing OLEDs of the present invention.

A substantially transparent substrate can comprise various suitable materials including, for example, polymeric components, glass, quartz and the like. Suitable polymeric components include, but are not limited to polyesters such as MYLAR®, polycarbonates, polyacrylates, polymethacrylates, polysulfones, and the like. Other substrate materials can also be selected provided, for example, that the materials can effectively support the other layers, and do not interfere with the device functional performance.

An opaque substrate can comprise various suitable materials including, for example, polymeric components like polyesters such as MYLAR®, polycarbonates, polyacrylates, polymethacrylates, polysulfones, and the like, which contain coloring agents or dyes such as carbon black. The substrate can also be comprised of silicon such as amorphous silicon, polycrystalline silicon, single crystal silicon, and the like. Another class of materials that can be used in the substrate are ceramics such as metallic compounds like metal oxides, halides, hydroxides, sulfides and others.

The substrate may have a thickness ranging for example from about 10 to about 5,000 micrometers, and more particularly from about 25 to about 1,000 micrometers.

An anode can comprise suitable positive charge injecting materials such as indium tin oxide (ITO), silicon, tin oxide, and metals with a work function ranging from about 4 eV to about 6 eV such as gold, platinum, and palladium. Other suitable materials for the anode include, but are not limited to, electrically conductive carbon, π-conjugated polymers such as polyaniline, polythiophene, polypyrrole, and the like having, for example, a work function equal to, or greater than, about 4 eV, and particularly from about 4 eV to about 6 eV. A substantially transparent anode can comprise, for example, indium tin oxide (ITO), very thin substantially transparent metallic layers, comprising a metal with a work function ranging from about 4 eV to about 6 eV such as gold, palladium and the like, having a thickness, for example, from about 10 Å to about 200 Å, and, particularly, from about 30 Å to about 100 Å. Additional suitable forms of the anode are disclosed in U.S. Pat. Nos. 4,885,211 and 5,703,436, which are incorporated herein by reference in their entirety. An anode can also comprise a metal-organic mixed layer (MOML) as disclosed in copending U.S. patent application Ser. No. 10/117,812 (D/A2091), which is incorporated herein by reference in its entirety. The thickness of the anode can range from about 10 Å to about 50,000 Å, with the preferred range depending on the electrical and optical constants of the anode material. One illustrative range of anode thickness is from about 300 Å to about 3,000 Å. Of course, a thickness outside of this range can also be used.

A cathode can comprise suitable electron injecting materials, such as metals, including high work function components, such as metals with, for example, a work function from about 4 eV to about 6 eV, or low work function components, such as metals with, for example, a work function of from about 2 eV to about 4 eV. The cathode can comprise a combination of a low work function (less than about 4 eV) metal and at least one other metal. Effective proportions of the low work function metal to the second or other metal are from less than about 0.1 weight percent to about 99.9 weight percent. Illustrative examples of low work function metals include, but are not limited to, alkaline metals such as lithium or sodium; Group 2A or alkaline earth metals such as beryllium, magnesium, calcium or barium; and Group III metals including rare earth metals and the actinide group metals such as scandium, yttrium, lanthanum, cerium, europium, terbium or actinium. Lithium, magnesium and calcium are preferred low work function metals. The Mg—Ag alloy cathodes described in U.S. Pat. No. 4,885,211, U.S. Pat. No. 4,720,432, and U.S. Pat. No. 5,703,436, the disclosures of which are totally incorporated herein by reference, are in embodiments preferred cathode materials for forming the cathodes Other specific cathodes are described in copending patent application comprise a metal-organic mixed later (MOML) as disclosed in U.S. patent application Ser. No. 10/117,812 (D/A2091), which is incorporated herein by reference in its entirety, and in U.S. Pat. No. 5,429,884, the disclosure of which is totally incorporated herein by reference. The cathodes can be formed from lithium alloys with other high work function metals such as aluminum and indium.

A substantially transparent cathode can comprise very thin substantially transparent metallic layers comprising a metal with a work function ranging from about 2 eV to about 4 eV, such as Mg, Ag, Al, Ca, In, Li and their alloys such as Mg:Ag alloys, comprised of, for example, from about 80 to 95 volume percent of Mg and about 20 to about 5 volume percent of Ag, and Li:Al alloys, comprised of, for example, from about 90 to 99 volume percent of Al, and from about 10 to about 1 volume percent of Li, and the like, having a thickness, for example, from about 10 Å to about 200 Å, and, particularly, from about 30 Å to about 100 Å. Of course, a thickness outside of this range can also be used.

The thickness of the cathode can range from, for example, about 10 nanometers to about 1,000 nanometers. Thicknesses outside of this range can also be used.

The anode and cathode used in the present OLEDs each may be a single layer or may comprise two, three or more layers. For instance, the electrode may be composed of a charge injection layer (i.e., an electron injection layer or a hole injection layer) and a capping layer. In embodiments, however, the charge injection layer may be considered distinct from the electrode.

An electron injecting layer can include very thin substantially transparent metallic layers, composed of a metal with a work function ranging from about 2 eV to about 4 eV, such as Mg, Ag, Al, Ca, In, Li and their alloys such as Mg:Ag alloys composed of, for example, from about 80 to 95 volume percent of Mg and about 20 to about 5 volume percent of Ag, and Li:Al alloys, composed of, for example, from about 90 to 99 volume percent of Al, and from about 10 to about 1 volume percent of Li, and the like, having a thickness, for example, from about 10 Å to about 200 Å, and, particularly, from about 30 Å to about 100 Å. Of course, a thickness outside of these ranges can also be used. The electron injection layer can also include very thin insulative materials such as an oxide material or an alkaline metal compound as described in U.S. Pat. Nos. 5,457,565; 5,608,287 and 5,739,635, which are each incorporated herein by reference in their entirety

A hole injecting layer can be composed of suitable positive charge injecting materials such as indium tin oxide (ITO), silicon, tin oxide, and metals with a work function ranging from about 4 eV to about 6 eV, such as, gold, platinum, and palladium. Other suitable materials for the hole injecting layer include, but are not limited to, electrically conductive carbon, $\pi$-conjugated polymers such as polyaniline, polythiophene, polypyrrole, and the like having, for example, a work function equal to, or greater than, about 4 eV, and particularly from about 4 eV to about 6 eV. A substantially transparent hole injecting material can be composed of very thin substantially transparent metallic layers, comprising a metal with a work function ranging from about 4 eV to about 6 eV, such as gold, palladium and the like, having a thickness, for example, from about 10 Å to about 200 Å, and, particularly, from about 30 Å to about 100 Å. Of course, a thickness outside of these ranges can also be used. Additional suitable forms of hole injecting layers are disclosed in U.S. Pat. Nos. 4,885,211 and 5,703,436, which are incorporated herein by reference in their entirety.

A capping layer on the anode and/or cathode can be included in order to increase the thermal stability, increase the environmental stability, and/or in some other way improve the performance of the organic light emitting device. An example of a capping layer that can be used to increase the thermal stability of the organic light emitting is a layer comprised of SiO, $SiO_2$, or mixtures thereof. Other examples are disclosed in copending applications U.S. Ser. No. 09/770,159 and U.S. Ser. No. 09/770,154, the disclosures of which are totally incorporated herein by reference. An example of a capping layer that can be used to increase the environmental stability of the organic light emitting device is a layer comprised of a stable metal such as Ag, Al, In, or Au. Another example of a capping layer that can be used to increase the environmental stability of the organic light emitting device is a layer comprised of a low work function metal as described for example in U.S. Pat. No. 5,059,861. The thickness of the capping layer can, for example, range from about 20 nanometers to about 5,000 nanometers. Typically, the thickness is from about 50 nanometers to 500 nanometers.

A buffer layer can be composed of a material with certain hole injection and transport properties and selected such that device performance is improved. Suitable materials that can be utilized in the buffer layer include semiconductive organic materials; such as, for example, porphyrin derivatives like 1,10,15,20-tetraphenyl-21H,23H-porphyrin copper (II) disclosed in U.S. Pat. No. 4,356,429, incorporated herein by reference in its entirety; copper phthalocyanine, copper tetramethyl phthalocyanine; zinc phthalocyanine; titanium oxide phthalocyanine; magnesium phthalocyanine; and the like, and wherein copper phthalocyanine is one preferred example. Mixtures of these and other suitable materials can also be used. Other suitable materials that can be utilized in the buffer layer include semiconductive and insulative metal compounds, such as for example metal oxides like MgO, $Al_2O_3$, BeO, BaO, AgO, SrO, SiO, $SiO_2$, $ZrO_2$, CaO, $Cs_2O$, $Rb_2O$, $Li_2O$, $K_2O$ and $Na_2O$; and metal halides, like LiF, KCl, NaCl, CsCl, CsF and KF. The buffer layer can have a thickness ranging from about 1 nm to about 100 nm. An illustrative thickness range for the buffer layer is from about 5 nm to about 25 nm. Another illustrative thickness range for the buffer layer is from about 1 nm to about 5 nm.

Illustrative anthracene derivative compounds include those disclosed in U.S. application Ser. No. 09/208,172 (corresponding to EP 1009044 A2), the disclosure of which is totally incorporated herein by reference, where there are disclosed anthracene derivative compounds of the following general structural formulas

I(A)(7)

I(A)(10)

I(A)(11)

I(A)(8)

I(A)(9)

wherein substituents $R^1$, $R^2$, $R^3$, $R^4$, $R^5$ and $R^6$ are each independently selected from the group consisting of: hydrogen; alkyl of from 1 to 24 carbon atoms; alkoxy of from 1 to 9 carbon atoms; triphenylsilyl; aryl of from 6 to 20 carbon atoms that is optionally substituted; heteroaryl of from 5 to 24 carbon atoms that is optionally substituted; halogen such as fluorine, chlorine, bromine; and cyano group. The hetero atom in the heteroaryl may be for example: nitrogen, sulfur, or oxygen. The aryl and heteroaryl are optionally substituted one, two or more times by the same or different moiety such as for example the following: alkyl of from 1 to 9 carbon atoms; alkoxy of from 1 to 9 carbon atoms; halogen such as fluorine, chlorine, bromine; and cyano group, and the like.

Other illustrative anthracene derivative compounds include those disclosed in U.S. Pat. No. 5,972,247, the disclosure of which is totally incorporated herein by reference, where there are disclosed anthracene derivative compounds of the following general structural formula

I(B)

wherein substituents R⁷, R⁸, R⁹, and R¹⁰ are each independently selected from the group consisting of:
Group 1: hydrogen, or alkyl of from 1 to 24 carbon atoms;
Group 2: aryl from 6 to 20 carbon atoms that is optionally substituted;
Group 3: carbon atoms necessary to complete a fused aromatic ring of naphthyl, anthracenyl, pyrenyl, or perylenyl;
Group 4: heteroaryl of from 5 to 24 carbon atoms that is optionally substituted;
Group 5: a fused heteroaromatic ring of furyl, thienyl, pyridyl, or quinolinyl;
Group 6: alkoxy, amino, alkyl amino, or aryl amino group of from 1 to 24 carbon atoms; and
Group 7: fluorine, chlorine, bromine or cyano.

The hetero atom in the heteroaryl may be for example: nitrogen, sulfur, or oxygen. The aryl and heteroaryl are optionally substituted one, two or more times by the same or different moiety such as for example the following: alkyl of from 1 to 9 carbon atoms; alkoxy of from 1 to 9 carbon atoms; halogen such as fluorine, chlorine, bromine; and cyano group, and the like.

Still other illustrative anthracene derivative compounds include those disclosed in U.S. Pat. No. 5,935,721, the disclosure of which is totally incorporated herein by reference, where there are disclosed anthracene derivative compounds of the following general structural formula

I(C)

wherein substituents R¹¹, R¹², R¹³, and R¹⁴ are each independently selected from the group consisting of:
Group 1: hydrogen, or alkyl of from 1 to 24 carbon atoms;
Group 2: aryl of from 6 to 20 carbon atoms that is optionally substituted;
Group 3: carbon atoms necessary to complete a fused aromatic ring of naphthyl, anthracenyl, pyrenyl, or perylenyl;
Group 4: heteroaryl of from 5 to 24 carbon atoms that is optionally substituted, carbon atoms necessary to complete a fused heteroaromatic ring of furyl, thienyl, pyridyl, quinolinyl, and other heterocyclic systems;
Group 5: alkoxy, amino, alkyl amino, or aryl amino group of from 1 to 24 carbon atoms; and
Group 6: fluorine, chlorine, bromine or cyano.

The hetero atom in the heteroaryl may be for example: nitrogen, sulfur, or oxygen. The aryl and heteroaryl are optionally substituted one, two or more times by the same or different moiety such as for example the following: alkyl of from 1 to 9 carbon atoms; alkoxy of from 1 to 9 carbon atoms; halogen such as fluorine, chlorine, bromine; and cyano group, and the like.

One preferred example of these anthracene derivative compounds of the general formula I(C) is 9,10-di-(2-naphthyl)anthracene derivative compound.

Yet, other examples of anthracene derivertive compounds include those disclosed in copending U.S. patent application Ser. No. 09/771,311 filed on Jan. 26, 2001, the disclosure of which is totally incorporated herein by reference, such as those illustrated by the following general formula

I(D)

wherein R¹⁵ and R¹⁶ are independently selected from the group consisting of hydrogen, an alkyl group with for example from 1 to about 6 carbon atoms, an aryl group with about 6 to about 30 carbon atoms. Specific examples of substituents for R¹⁵ and R¹⁶ are hydrogen, methyl, tert-butyl, a phenyl, a naphthyl, and the like; X and Y are independently selected from the group consisting of hydrogen, an alkyl group with for example from 1 to about 6 carbon atoms, an aryl group with about 6 to about 30 carbon atoms, an alkoxy group with for instance from 1 to about 6 carbon atoms, a halogen, a cyano group and the like. Specific examples of substituents for X and Y are hydrogen, methyl, tert-butyl, tert-butoxy and the like.

Examples of triazine derivative compounds include those disclosed in U.S. Pat. Nos. 6,229,012, 6,225,467 and 6,057,048, the disclosures of which are totally incorporated herein by reference. Exemplary triazine derivative compounds are for instance encompassed by the following structural formulas

II(A)

II(B)

-continued

II(C)

II(D)

wherein $Ar^1$, $Ar^2$, $Ar^3$, and $Ar^4$ are each independently aryl of from 6 to about 20 carbon atoms that is optionally substituted, and the aryl can be selected, for example, from the group consisting of a phenyl, a stilbenyl, a biphenylyl, a naphthyl, a pyridyl, and a quinolyl and the like. The aryl group is optionally substituted one, two, or more times by a substituent selected from the group consisting of an alkyl group with for example, from 1 to about 6 carbon atoms, an alkoxy group with, for example, from 1 to about 6 carbon atoms, a dialkylamino group with, for example, from 1 to about 3 carbon atoms, a halogen, a cyano group, and the like;

$R^{17}$ to $R^{18}$ are substituents independently selected from the group consisting of hydrogen, aliphatic such as an alkyl group with, for example, from 1 to about 6 carbon atoms, an alkoxy group with for example, from 1 to about 6 carbon atoms, a halogen such as chloride, a cyano group;

L is a divalent group which may be selected from the group consisting of —C(R'R")—, an ethylene, —Si (R'R")—, an oxygen atom, a sulfur atom, and the like, wherein R' and R" are each independently a hydrogen atom, an alkyl group containing from 1 to about 10 carbon atoms, or an alkoxyl group containing from 1 to about 10 carbon atoms.

The luminescent region, particularly the light emitting zone, can further include from about 0.01 weight percent to about 25 weight percent (based on the weight of the light emitting zone) of a luminescent material as a dopant. Examples of dopant materials that can be utilized in the luminescent region are fluorescent materials, such as coumarin, dicyanomethylene pyranes, polymethine, oxabenzanthrane, xanthene, pyrylium, carbostyl, perylene, and the like. Another preferred class of fluorescent materials are quinacridone dyes. Illustrative examples of quinacridone dyes include quinacridone, 2-methylquinacridone, 2,9-dimethylquinacridone, 2-chloroquinacridone, 2-fluoroquinacridone, 1,2-benzoquinacridone, N,N'-dimethylquinacridone, N,N'-dimethyl-2-methylquinacridone, N,N'-dimethyl-2,9-dimethylquinacridone, N,N'-dimethyl-2-chloroquinacridone, N,N'-dimethyl-2-fluoroquinacridone, N,N'-dimethyl-1,2-benzoquinacridone, and the like as disclosed in U.S. Pat. Nos. 5,227,252; 5,276,381 and 5,593,788, each incorporated herein by reference in its entirety. Another class of fluorescent materials that may be used is fused ring fluorescent dyes. Exemplary suitable fused ring fluorescent dyes include perylene, rubrene, anthracene, coronene, phenanthrecene, pyrene and the like, as disclosed in U.S. Pat. No. 3,172,862, which is incorporated herein by reference in its entirety. Also, fluorescent materials include butadienes, such as 1,4-diphenylbutadiene and tetraphenylbutadiene, and stilbenes, and the like, as disclosed in U.S. Pat. Nos. 4,356,429 and 5,516,577, each incorporated herein by reference in its entirety. Other examples of fluorescent materials that can be used are those disclosed in U.S. Pat. No. 5,601,903, which is incorporated herein by reference in its entirety.

Additionally, luminescent dopants that can be utilized in the luminescent region are the fluorescent dyes disclosed in U.S. Pat. No. 5,935,720 (which is incorporated herein by reference in its entirety) such as 4-(dicyanomethylene)-2-I-propyl-6-(1,1,7,7-tetramethyljulolidyl-9-enyl)-4H-pyran (DCJTB); the lanthanide metal chelate complexes, such as for example, tris(acety lacetonato)(phenanthroline) terbium, tris(acetyl acetonato)(phenanthroline)europium, and tris (thenoyl trisfluoroacetonato)(phenanthroline)europium, and those disclosed in Kido et al., "White light emitting organic electroluminescent device using lanthanide complexes," Jpn. J. Appl. Phys., Volume 35, pp. L394–L396 (1996), which is incorporated herein by reference in its entirety; and phosphorescent materials, such as organometallic compounds containing heavy metal atoms that lead to strong spin-orbit coupling, such as those disclosed in Baldo et.al., "Highly efficient organic phosphorescent emission from organic electroluminescent devices," Letters to Nature, Volume 395, pp. 151–154 (1998), which is incorporated herein by reference in its entirety. Preferred examples include 2,3,7,8,12,13,17,18-octaethyl-21H23H-phorpine platinum (II) (PtOEP) and fac tris(2-phenylpyridine)iridium(Ir $(ppy)_3$).

In addition to a triazine derivative material and an anthracene derivative material, the luminescent region, particularly the hole transport zone can also include one or more other materials with hole transporting properties. Examples of hole-transporting materials that can be utilized in the luminescent region include polypyrrole, polyaniline, poly (phenylene vinylene), polythiophene, polyarylamine as disclosed in U.S. Pat. No. 5,728,801, which is incorporated herein by reference in its entirety, and their derivatives, and known semiconductive organic materials; porphyrin derivatives such as 1,10,15,20-tetraphenyl-21H,23H-porphyrin copper (II) disclosed in U.S. Pat. No. 4,356,429, incorporated herein by reference in its entirety; copper phthalocyanine, copper tetramethyl phthalocyanine; zinc phthalocyanine; titanium oxide phthalocyanine; magnesium phthalocyanine; and the like A specific class of hole transporting materials that can be utilized in the luminescent region are the aromatic tertiary amines such as those disclosed in U.S. Pat. No. 4,539,507, which is incorporated herein by reference in its entirety. Suitable exemplary aromatic tertiary amines include, but are not limited to, bis(4-dimethylamino-2-methylphenyl)phenylmethane, N,N,N-tri(p-tolyl)amine, 1,1-bis(4-di-p-tolylaminophenyl)cyclohexane, 1,1-bis(4-di-p-tolylaminophenyl)-4-phenylcyclohexane, N,N'-diphenyl-N,N'-bis(3-methylphenyl)-1,1'-biphenyl-4,4'-diamine, N,N'-diphenyl-N,N'-bis(3-methylphenyl)-1,1'-biphenyl-4,4'-diamine, N,N'-diphenyl-N,N'-bis(4-methoxyphenyl)-1,1'-biphenyl-4,4'-diamine, N,N,N',N'-tetra-p-tolyl-1,1'-biphenyl-4,4'-diamine, N,N'-di-1-naphthyl-N,N'-diphenyl-1,1'-biphenyl-4,4'-diamine, N,N'-bis(p-biphenyl)-N,N'-diphenyl benzidine(biphenyl TPD), mixtures thereof and the like. A preferred class of tertiary aromatic amines that can be used in the luminescent region are the naphtyl-substituted benzidine derivatives, such as, N,N'-di(naphthalene-1-yl)-N,N'-diphenyl-benzidine (NPB). Another class of aromatic tertiary amines are polynuclear aromatic amines. Examples of these polynuclear aromatic amines include, but are not limited to, N,N-bis-[4'-(N-phenyl-N-m-tolylamino)-4-biphenylyl] aniline; N,N-bis-[4'-(N-phenyl-N-m-tolylamino)-4-biphenylyl]-m-toluidine; N,N-bis-[4'-(N-phenyl-N-m-tolylamino)-4-biphenylyl]-p-toluidine; N,N-bis-[4'-(N-phenyl-N-p-tolylamino)-4-biphenylyl]aniline; N,N-bis-[4'-(N-phenyl-N-p-tolylamino)-4-biphenylyl]-m-toluidine; N,N-bis-[4'-(N-phenyl-N-p-tolylamino)-4-biphenylyl]-p-toluidine; N,N-bis-[4'-(N-phenyl-N-p-chlorophenylamino)-4-biphenylyl]-m-toluidine; N,N-bis-[4'-(N-phenyl-N-m-chlorophenylamino)-4-biphenylyl]-m-toluidine; N,N-bis-[4'-(N-phenyl-N-m-chlorophenylamino)-4-biphenylyl]-p-toluidine; N,N-bis-[4'-(N-phenyl-N-m-tolylamino)-4-biphenylyl]-p-chloroaniline; N,N-bis-[4'-(N-phenyl-N-p-tolylamino)-4-biphenylyl]-m-chloroaniline; N,N-bis-[4'-(N-phenyl-N-m-tolylamino)-4-biphenylyl]-1-aminonaphthalene, mixtures thereof and the like; 4,4'-bis(9-carbazolyl)-1,1'-biphenyl compounds, such as 4,4'-bis(9-carbazolyl)-1,1'-biphenyl and 4,4'-bis(3-methyl-9-carbazolyl)-1,1'-biphenyl, and the like.

A specific class of the hole transporting materials that can be used in the luminescent region are the indolo-carabazoles, such as those disclosed in U.S. Pat. Nos. 5,942,340 and 5,952,115, each incorporated herein by reference in its entirety, such as 5,11-di-naphthyl-5,11-dihydroindolo[3,2-b] carbazole, and 2,8-dimethyl-5,11-di-naphthyl-5,11-dihydroindolo[3,2-b]carbazole; N,N,N'N'-tetraarylbenzidines, wherein aryl may be selected from phenyl, m-tolyl, p-tolyl, m-methoxyphenyl, p-methoxyphenyl, 1-naphthyl, 2-naphthyl and the like. Illustrative examples of N,N,N'N'-tetraarylbenzidine are N,N;-di-1-naphthyl-N,N'-diphenyl-1,1'-biphenyl-4,4'-diamine, which is more preferred; N,N'-bis(3-methylphenyl)-N,N'-diphenyl-1,1'-biphenyl-4,4'-diamine; N,N'-bis(3-methoxyphenyl)-N,N'-diphenyl-1,1'-biphenyl-4,4'-diamine, and the like.

In embodiments, the luminescent region can include one or more non-anthracene and non-triazine derivative compounds which have the desired properties such as electron transporting and/or light emitting properties. In embodiments, a number of the following exemplary non-anthracene and non-triazine derivative compounds may have electron transporting and/or light emitting properties and thus may be useful in the luminescent region (in for example the light emitting zone and/or the electron transport zone): polyfluorenes, such as poly(9,9-di-n-octylfluorene-2,7-diyl), poly(2,8-(6,7,12,12-tetraalkylindenofluorene) and copolymers containing fluorenes such as fluorene-amine copolymers, as disclosed in incorporated Bernius et al., Proceedings of SPIE Conference on Organic Light Emitting Materials and Devices III, Denver, Colo., July 1999, Volume 3797, p. 129.

Other suitable non-anthracene and non-triazine derivative compounds may include metal oxinoids as disclosed in U.S. Pat. Nos. 4,539,507; 5,151,629; 5,150,006, 5,141,671, and 5,846,666, the disclosures of each being totally incorporated herein by reference. Illustrative specific examples include tris(8-hydroxyquinolinate)aluminum ($Alq_3$), bis(8-hydroxyquinolato)-(4-phenylphenolato)aluminum (Balq). Other examples include tris(8-hydroxyquinolinate)gallium, bis(8-hydroxyquinolinate)magnesium, bis(8-hydroxyquinolinate) zinc, tris(5-methyl-8-hydroxyquinolinate)aluminum, tris(7-propyl-8-quinolinolato)aluminum, bis[benzo{f}-8-quinolinate]zinc, bis(10-hydroxybenzo[h]quinolinate) beryllium, and the like.

Another suitable class of non-anthracene and non-triazine derivative compounds is stilbene derivatives, such as those disclosed in U.S. Pat. No. 5,516,577, the disclosure of which is totally incorporated herein by reference. Further examples of non-anthracene and non-triazine derivative compounds are the metal thioxinoid compounds, illustrated in U.S. Pat. No. 5,846,666, the disclosure of which is totally incorporated herein by reference, such as metal thioxinoid compounds of bis(8-quinolinethiolato)zinc, bis(8-quinolinethiolato)cadmium, tris(8-quinolinethiolato)gallium, tris(8-quinolinethiolato)indium, bis(5-methylquinolinethiolato) zinc, tris(5-methylquinolinethiolato)gallium, tris(5-methylquinolinethiolato)indium, bis(5-methylquinolinethiolato)cadmium, bis(3-methylquinolinethiolato)cadmium, bis(5-methylquinolinethiolato)zinc, bis[benzo{f}-8-quinolinethiolato]zinc, bis[3-methylbenzo{f}-8-quinolinethiolato]zinc, bis[3,7-dimethylbenzo{f}-8-quinolinethiolato]zinc, and the like. Specific non-anthracene and non-triazine derivative compounds are bis(8-quinolinethiolato)zinc, bis(8-quinolinethiolato)cadmium, tris(8-quinolinethiolato)gallium, tris(8-quinolinethiolato)indium and bis[benzo{f}-8-quinolinethiolato]zinc. Other suitable non-anthracene and non-triazine derivative compounds are the oxadiazole metal chelates disclosed in incorporated U.S. Pat. No. 5,925,472, which materials include bis[2-(2-hydroxyphenyl)-5-phenyl-1,3,4-oxadiazolato]zinc; bis[2-(2-hydroxyphenyl)-5-phenyl-1,3,4-oxadiazolato]beryllium; bis [2-(2-hydroxyphenyl)-5-(1-naphthyl)-1,3,4-oxadiazolato] zinc; bis[2-(2-hydroxyphenyl)-5-(1-naphthyl)-1,3,4-oxadiazolato]beryllium; bis[5-biphenyl-2-(2-hydroxyphenyl)-1,3,4-oxadiazolato]zinc; bis[5-biphenyl-2-(2-hydroxyphenyl)-1,3,4-oxadiazolato]beryllium; bis(2-hydroxyphenyl)-5-phenyl-1,3,4-oxadiazolato]lithium; bis [2-(2-hydroxyphenyl)-5-p-tolyl-1,3,4-oxadiazolato]zinc; bis [2-(2-hydroxyphenyl)-5-p-tolyl-1,3,4-oxadiazolato] beryllium; bis[5-(p-tert-butylphenyl)-2-(2-hydroxyphenyl)-1,3,4-oxadiazolato]zinc; bis[5-(p-tert-butylphenyl)-2-(2-hydroxyphenyl)-1,3,4-oxadiazolato]beryllium; bis[2-(2-hydroxyphenyl)-5-(3-fluorophenyl)-1,3,4-oxadiazolato] zinc; bis[2-(2-hydroxyphenyl)-5-(4-fluorophenyl)-1,3,4-oxadiazolato]zinc; bis[2-(2-hydroxyphenyl)-5-(4-fluorophenyl)-1,3,4-oxadiazolato]beryllium; bis[5-(4-chlorophenyl)-2-(2-hydroxyphenyl)-1,3,4-oxadiazolato] zinc; bis[2-(2-hydroxyphenyl)-5-(4-methoxyphenyl)-1,3,4-oxadiazolato]zinc; bis[2-(2-hydroxy-4-methylphenyl)-5-phenyl-1,3,4-oxadiazolato]zinc; bis[2-α-(2-hydroxynaphthyl)-5-phenyl-1,3,4-oxadiazolato]zinc; bis[2-(2-hydroxyphenyl)-5-p-pyridyl-1,3,4-oxadiazolato]zinc; bis [2-(2-hydroxyphenyl)-5-p-pyridyl-1,3,4-oxadiazolato] beryllium; bis[2-(2-hydroxyphenyl)-5-(2-thiophenyl)-1,3,4-oxadiazolato]zinc; bis[2-(2-hydroxyphenyl)-5-phenyl-1,3,4-thiadiazolato]zinc; bis[2-(2-hydroxyphenyl)-5-phenyl-1,3,4-thiadiazolato]beryllium; bis[2-(2-hydroxyphenyl)-5-(1-naphthyl)-1,3,4-thiadiazolato]zinc; and bis[2-(2-hydroxyphenyl)-5-(1-naphthyl)-1,3,4-thiadiazolato] beryllium, and the like. Another suitable class of non-anthracene and non-triazine derivative compounds are the quinolines, such as, for example, 1,4-bis(4-phenylquinolin-2-yl)benzene, 4,4'-bis(4-phenylquinolin-2-yl)-1,1'-biphenyl (TA).

In embodiments where the luminescent region includes one or more hole transport material and/or one or more electron transport material in addition to the organic electroluminescent material(s), the organic electroluminescent material, the hole transport material(s), and/or the electron transport material(s) can be formed in separate layers, such as the OLEDs disclosed in U.S. Pat. Nos. 4,539,507; 4,720,432 and 4,769,292; or in the same layer thus forming mixed areas of two or more materials, such as the OLEDs disclosed in U.S. Pat. Nos. 5,853,905; 5,925,980; 6,130,001; 6,114,055; 6,392,250; 6,392,339; and U.S. patent application Ser. No. 09/770,159, filed on Jan. 26, 2001. The disclosures of these patents and patent applications are incorporated herein by reference in their entirety.

The thickness of the luminescent region can vary for example, from about 10 Å to about 10,000 Å, typically from about 200 Å to about 2,000 Å, and particularly from about 500 Å to about 1,500 Å. In embodiments wherein the luminescent region includes two or more layers, the thickness of each layer can, for example, be from about 10 Å to about 5,000 Å, typically from about 50 Å to about 2,000 Å, and particularly from about 100 Å to about 1,500 Å.

Each layer of the OLED may have a generally uniform or non-uniform composition across the layer thickness where each layer is composed entirely of one material or a mixture of materials.

The OLED can be fabricated by sequentially forming the desired layers on the substrate using any suitable thin film forming technique, typically, spin coating or deposition by thermal evaporation in vacuum. More details about fabrication and operation of organic light emitting devices are disclosed, for example, in U.S. Pat. Nos. 4,539,507 and 4,769,292, and in copending U.S. applications Ser. No. 09/357,551, filed on Jul. 20, 1999; Ser. No. 09/606,670, filed on Jun. 30, 2000; and Ser. No. 09/770,159, filed on Jan. 26, 2001, the disclosure of each patent and patent application being totally incorporated herein by reference.

Organic light emitting device according to this invention can demonstrate an improved performance, such as, a higher operational stability and improved color purity, compared to other blue-emitting OLEDs, such as, for example, OLEDs containing an anthracene derivative compound as an emitting material and a quinoline-type metal chelate derivative compound (which is not a triazine derivative compound) as an electron transport material.

The invention will now be described in detail with respect to specific preferred embodiments thereof, it being understood that these examples are intended to be illustrative only and the invention is not intended to be limited to the materials, conditions, or process parameters recited herein. All percentages and parts are by weight unless otherwise indicated.

EXAMPLE 1

An Organic Light Emitting Device Comprising an Anthracene Derivative Compound in the Light Emitting Zone and a Triazine Derivative Compound in the Electron Transport Zone An organic light emitting device (referred to herein as device A) of structure ITO anode (50 nm)/CuPc porphyrin compound buffer layer (15 nm)/NPB tertiary aromatic amine compound hole transport layer (30 nm)/BH2 anthracene derivative compound emitter layer (30 nm)/T1 triazine derivative compound electron transport layer (20 nm)/Mg:Ag cathode (9:1 volume ratio of Mg:Ag, 200 nm) was fabricated. The molecular structures of CuPc, NPB, BH2 and T1 are as follows:

CuPc

NPB

BH2

T1

The device was fabricated by vacuum deposition at a base pressure of $5 \times 10^{-6}$ torr., where all organic layers, and the cathode were thermally evaporated, on ITO-coated glass substrates, pre-cleaned using UV-ozone cleaning.

On driving using a current of density=31.25 mA/cm$^2$, the device produced blue emission at an intensity of 240 cd/m$^2$ and a color purity corresponding to (0.144, 0.083) coordinates on the CIE chart. The driving voltage needed to operate the device at these conditions was 8.7 volts. After 60 hours of continuous operation at this current density in a nitrogen atmosphere, the decay in emission intensity was less than 1% of the initial intensity.

COMPARATIVE EXAMPLE 1 (PRIOR ART)

An Organic Light Emitting Device Comprising an Anthracene Derivative Compound in the Light Emitting Zone and Quinoline-Type Metal Chelate Derivative Compound (which is not a Triazine Derivative Compound) in the Electron Transport Zone An organic light emitting device (referred to herein as device B) of structure ITO anode (50 nm)/CuPc porphyrin compound buffer layer (15 nm)/NPB tertiary aromatic amine compound hole transport layer (30 nm)/BH2 anthracene derivative compound emitter layer (30 nm)/AlQ$_3$ quinoline-type metal chelate derivative compound electron transport layer (20 nm)/Mg:Ag cathode (9:1 volume ratio of Mg:Ag, 200 nm). The molecular structure of AlQ$_3$ is AlQ$_3$ The molecular structures of all other organic compounds were given in the previous example.

The device was fabricated by vacuum deposition at a base pressure of 5×10$^{-6}$ torr., where all organic layers, and the cathode were thermally evaporated, on ITO-coated glass substrates, pre-cleaned using UV-ozone cleaning.

On driving using a current of density=31.25 mA/cm$^2$, the device produced blue emission at an intensity of 390 cd/m$^2$ and a color purity corresponding to (0.154, 0.114) coordinates on the CIE chart. The driving voltage needed to operate the device at these conditions was 8.3 volts. After 60 hours of continuous operation at this current density in a nitrogen atmosphere, the decay in emission intensity was about 10% of the initial intensity.

Comparing performance of devices A (this invention) and B (prior art), it is clear that device A showed higher color purity as evident from the smaller values for the CIE coordinates, especially, the "y" (i.e., second) coordinate. In fact, the high color purity of device A satisfied NTSC industry standards (NTSC standards for blue coordinates are (0.14, 0.08)). Obviously, device B does not meet these standards. In addition to the higher color purity, device A demonstrated an increased operational stability compared to device B. Blue-emitting OLEDs, according to this invention, are therefore more suitable for potential technological applications compared to prior art devices, as they are able to provide better performance.

EXAMPLE 2

An Organic Light Emitting Device Comprising Anthracene Derivative Compound in the Light Emitting Zone and Triazine Derivative Compound in the Electron Transport Zone An organic light emitting device (referred to herein as device C) of structure ITO anode (50 nm)/NPB tertiary aromatic amine compound hole transport layer (30 nm)/SBPA anthracene derivative compound emitter layer (42 nm)/TBT triazine derivative compound first electron transport layer (10 nm)/AlQ$_3$ quinoline derivative compound second electron transport layer (20 nm)/Mg:Ag cathode (9:1 volume ratio of Mg:Ag, 200 nm) was fabricated. The molecular structures of SBPA and TBT are as follows:

SBPA

TBT

Structures of other organic compounds were given in the previous examples.

The device was fabricated by vacuum deposition at a base pressure of 5×10$^{-6}$ torr., where all organic layers, and the cathode were thermally evaporated, on ITO-coated glass substrates, pre-cleaned using UV-ozone cleaning.

On driving using a current of density=25.00 mA/cm$^2$, the device produced blue emission at an intensity of 451 cd/m$^2$ and a color purity corresponding to (0.158, 0.149) coordinates on the CIE chart. The driving voltage needed to operate the device at these conditions was 10.3 volts.

COMPARATIVE EXAMPLE 2 (PRIOR ART)

An Organic Light Emitting Device Comprising Anthracene Derivative Compound in the Light Emitting Zone and Quinoline-Type Metal Chelate Derivative Compound (which is not a Triazine Derivative Compound) in the Electron Transport Zone An organic light emitting device (referred to herein as device D) of structure ITO anode (50 nm)/NPB tertiary aromatic amine compound hole transport layer (30 nm)/SBPA anthracene derivative compound emitter layer (42 nm)/AlQ$_3$ quinoline derivative compound electron transport layer (20 nm)/Mg:Ag cathode (9:1 volume ratio of Mg:Ag, 200 nm) was fabricated.

Structures of the organic compounds were given in the previous examples.

The device was fabricated by vacuum deposition at a base pressure of 5×10$^{-6}$ torr., where all organic layers, and the cathode were thermally evaporated, on ITO-coated glass substrates, pre-cleaned using UV-ozone cleaning.

On driving using a current of density=25.00 mA/cm$^2$, the device produced blue emission at an intensity of 322 cd/m$^2$ and a color purity corresponding to (0.189, 0.261) coordinates on the CIE chart. The driving voltage needed to operate the device at these conditions was 9.3 volts.

Comparing performance of devices C (this invention) and D (prior art), it is clear that device C showed higher color purity as evident from the smaller values for the CIE coordinates, especially, the "y" (i.e., second) coordinate.

In addition, devices A and C illustrate that the improved performance of devices according to embodiments of this invention is not limited to a specific anthracene derivative compound or a specific triazine derivative compound. Rather utilizing a variety of anthracene derivative compounds and triazine derivative compounds can be used to produce organic light emitting devices with improved performance.

EXAMPLE 3

An Organic Light Emitting Device Comprising an Anthracene Derivative Compound and Another Luminescent Material in the Light Emitting Zone and a Triazine Derivative Compound in the Electron Transport Zone An organic light emitting device (referred to herein as device E) of structure ITO anode (50 nm)/NPB tertiary aromatic amine compound hole transport layer (30 nm)/SBPA anthracene derivative compound doped with acridone blue luminescent material (1.6% by volume of the emitter layer) emitter layer (42 nm)/TBT triazine derivative compound first electron transport layer (10 nm)/AlQ$_3$ quinoline derivative compound second electron transport layer (20 nm)/Mg:Ag cathode (9:1 volume ratio of Mg:Ag, 200 nm) was fabricated.

The molecular structure of acridone blue luminescent material is

Acridone blue luminescent material

Structures of other organic compounds were given in the previous examples.

The device was fabricated by vacuum deposition at a base pressure of 5×10$^{-6}$ torr., where all organic layers, and the cathode were thermally evaporated, on ITO-coated glass substrates, pre-cleaned using UV-ozone cleaning.

On driving using a current of density=25.00 mA/cm$^2$, the device produced blue emission at an intensity of 410 cd/m$^2$ and a color purity corresponding to (0.158, 0.112) coordinates on the CIE chart. The driving voltage needed to operate the device at these conditions was 10.4 volts.

From a comparison of the color purity coordinates of devices C and E, it can be seen that the color purity of devices according to this invention can be further improved by adding a blue luminescent material in the luminescent zone.

EXAMPLE 4

An Organic Light Emitting Device Comprising a Mixture of an Anthracene Derivative Compound and a Triazine Derivative Compound in the Light Emitting Zone and a Triazine Derivative Compound in the Electron Transport Zone A group of organic light emitting devices (referred to herein as devices F–i through F–iii)) of structure ITO anode (50 nm)/CuPc porphyrin compound buffer layer (15 nm)/NPB tertiary aromatic amine compound hole transport layer (30 nm)/A first layer (2 nm) of the emitting zone composed of SBPA, and a second layer (35 nm) of the emitting zone composed of a mixture of SBPA anthracene derivative compound and TBT triazine derivative compound/TBT triazine derivative compound first electron transport layer (8 nm)/T1 triazine derivative compound second electron transport layer (25 nm)/Mg:Ag cathode (9:1 volume ratio of Mg:Ag, 200 nm) was fabricated.

Molecular Structures of the organic compounds were given in the previous examples.

In device F-i, the SBPA:TBT ratio in the second layer of the emitting zone was (100:0 by volume, i.e., no TBT); in device F-ii, the SBPA:TBT ratio in the second layer of the emitting zone was (95:5 by volume); and in device F-iii, the SBPA:TBT ratio in the second layer of the emitting zone was (75:25 by volume).

The devices were fabricated by vacuum deposition at a base pressure of 5×10$^{-6}$ torr., where all organic layers, and the cathode were thermally evaporated, on ITO-coated glass substrates, pre-cleaned using UV-ozone cleaning.

After continuous driving for 100 hours at a current of density=31.25 mA/cm², the intensity of devices F-i, F-ii, and F-iii devices decreased by 40%, 30% and 23% of the initial intensity.

Therefore, it can be seen that using a mixture of an anthracene derivative compound and a triazine derivative compound in the light emitting zone can further improve the performance of devices according to this invention, and specifically, can increase their operational stability. It can also be seen that certain mixing ratios can lead to further increase in device operational stability over other ratios.

EXAMPLE 5

An Organic Light Emitting Device Comprising a Mixture of an Anthracene Derivative Compound and a Charge Transport Material in the Light Emitting Zone, and an Anthracene Derivative Compound and a Triazine Derivative Compound in the Electron Transport Zone An organic light emitting devices (referred to herein as device G) of structure ITO anode (50 nm)/CuPc porphyrin compound buffer layer (15 nm)/NPB tertiary aromatic amine compound hole transport layer (50 nm)/A mixture of BH2 anthracene derivative compound and NPB tertiary aromatic amine charge transport compound (1:1 by volume) light emitting layer (25 nm)/A first layer (5 nm) of electron transport zone composed of BH2 anthracene derivative compound, and a second layer (20 nm) of electron transport zone composed of T1 triazine derivative compound/Mg:Ag cathode (9:1 volume ratio of Mg:Ag, 200 nm) was fabricated.

Molecular structures of the organic compounds were given in the previous examples.

The device was fabricated by vacuum deposition at a base pressure of $5 \times 10^{-6}$ torr., where all organic layers, and the cathode were thermally evaporated, on ITO-coated glass substrates, pre-cleaned using UV-ozone cleaning.

On driving using a current of density=31.25 mA/cm², the device produced blue emission at an intensity of 200 cd/m² and a color purity corresponding to (0.145, 0.108) coordinates on the CIE chart. The driving voltage needed to operate the device at these conditions was 8.1 volts. After 600 hours of continuous operation at this current density in a nitrogen atmosphere, the decay in emission intensity was only about 10% of the initial intensity.

Therefore, it can be seen that using a mixture of an anthracene derivative compound and a charge transport material in the light emitting zone together with an anthracene derivative compound and a triazine derivative compound in the electron transport zone can provide blue organic light emitting devices with pure blue emission and excellent operational stability

From the above examples, it can be concluded that blue-emitting OLEDs, according to this invention, are more suitable for potential technological applications, as they are able to provide better performance compared to other blue-emitting OLEDs.

We claim:

1. A device comprising:
   an anode;
   a cathode; and
   a luminescent region between the cathode and the anode, wherein the luminescent region comprises an anthracene derivative compound, a triazine derivative compound, and an additional anthracene or triazene derivative compound, wherein the anthracene derivative compounds are selected from the group consisting of formula I(A)(4) and of formula I(D):

wherein substituents $R^1$, $R^2$, $R^3$, and $R^4$ are each independently selected from the group consisting of: hydrogen; alkyl of from 1 to 24 carbon atoms; alkoxy of from 1 to 9 carbon atoms; triphenylsilyl; aryl of from 6 to 20 carbon atoms that is optionally substituted; heteroaryl of from 5 to 24 carbon atoms that is optionally substituted; halogen; and cyano group;

wherein $R^{15}$ and $R^{16}$ are independently selected from the group consisting of hydrogen, an alkyl group with from 1 to about 6 carbon atoms, an aryl group with about 6 to about 30 carbon atoms;

wherein X and Y are independently selected from the group consisting of hydrogen, an alkyl group with from 1 to about 6 carbon atoms, an aryl group with about 6 to about 30 carbon atoms, an alkoxy group with from 1 to about 6 carbon atoms, a halogen, a cyan group wherein the triazine derivative compounds are selected from the group consisting of formula II(A) and of formula II(B):

wherein Ar¹, Ar², AR³, and Ar⁴ are each independently aryl of from 6 to about 20 carbon atoms that is optionally substituted;

wherein $R^{17}$ to $R^{18}$ are independently selected from the group consisting of hydrogen, an aliphatic with from 1 to about 6 carbon atoms, an alkoxy group with from 1 to about 6 carbon atoms, a halogen, a cyano group.

2. The device of claim 1, wherein the luminescent region includes (a) a light emitting zone comprising at least one of the anthracene derivative compounds; and (b) an electron transport zone comprising at least one of the triazine derivative compounds.

3. The device of claim 1, wherein the luminescent region includes (a) a light emitting zone comprising at least one of the anthracene derivative compounds at least one of and the triazine derivative compounds; and (b) an electron transport zone.

4. The device of claim 1, wherein the luminescent region includes at least two triazine derivative compounds, resulting in a first triazine derivative compound and a second triazine derivative compound that are the same or different from each other, wherein the luminescent region comprises (a) a light emitting zone comprising at least one of the anthracene derivative compound and the first triazine derivative compound; and (b) an electron transport zone comprising the second triazine derivative compound.

5. The device of claim 1, wherein the luminescent region includes at least two anthracene derivative compounds and at least two triazine derivative compounds, resulting in a first anthracene derivative compound and a second anthracene derivative compound that are the same or different from each other as well as a first triazine derivative compound and a second triazine derivative compound that are the same or different from each other, wherein the luminescent region comprises (a) a light emitting zone comprising the first anthracene derivative compound and the first triazine derivative compound; and (b) an electron transport zone comprising the second anthracene derivative compound and the second triazine derivative compound.

6. The device of claim 1, wherein the luminescent region includes at least two anthracene derivative compounds, resulting in a first anthracene derivative compound and a second anthracene derivative compound that are the same or different from each other, wherein the luminescent region comprises (a) a light emitting zone comprising the first anthracene derivative compound; and (b) an electron transport zone comprising the second anthracene derivative compound and at least one of the triazine derivative compounds.

7. The device of claim 1, wherein the luminescent region includes at least two anthracene derivative compounds and at least two triazine derivative compounds, resulting in a first anthracene derivative compound and a second anthracene derivative compound that are the same or different from each other as well as a first triazine derivative compound and a second triazine derivative compound that are the same or different from each other, wherein the luminescent region comprises (a) a light emitting zone comprising the first anthracene derivative compound; and (b) an electron transport zone comprising (i) a first layer including the second anthracene derivative compound and the first triazine derivative compound, and (ii) a second layer including the second triazine derivative compound.

8. The device of claim 1, wherein the luminescent region includes at least two anthracene derivative compounds, resulting in a first anthracene derivative compound and a second anthracene derivative compound that are the same or different from each other, wherein the luminescent region comprises (a) a light emitting zone comprising the first anthracene derivative compound; and (b) an electron transport zone comprising (i) a first layer including the second anthracene derivative compound and at least one of the triazine derivate compounds, and (ii) a second layer.

9. The device of claim 1, wherein the luminescent region includes at least two anthracene derivative compounds and at least two triazme derivative compounds, resulting in a first anthracene derivative compound and a second anthracene derivative compound that are the same or different from each other as well as a first triazine derivative compound and a second triazine derivative compound that are the same or different from each other, wherein the luminescent region comprises (a) a hole transport zone comprising the first anthracene derivative compound; (b) a light emitting zone comprising the second anthracene derivative compound and the first triazine derivative compound; and (c) an electron transport zone comprising the second triazine derivative compound.

10. The device of claim 1, wherein the luminescent region includes at least two anthracene derivative compounds, resulting in a first anthracene derivative compound and a second anthracene derivative compound that are the same or different from each other, wherein the luminescent region comprises (a) a hole transport zone comprising the first anthracene derivative compound; (b) a light emitting zone comprising the second anthracene derivative compound and at least one of the triazine derivative compounds; and (c) an electron transport zone.

11. The device of claim 1, wherein the luminescent region includes at least two anthracene derivative compounds resulting in a first anthracene derivative compound and a second anthracene derivative compound that are the same or different from each other, wherein the luminescent region comprises (a) a hole transport zone comprising the first anthracene derivative compound; (b) a light emitting zone comprising the second anthracene derivative compound and at least one of the triazine derivative compounds.

12. The device of claim 1, wherein the luminescent region comprises (a) a hole transport zone comprising at least one of the anthracene derivative compounds; (b) a light emitting zone comprising at least one of the triazine derivative compounds.

13. The device of claim 1, wherein the luminescent region includes at least two triazine derivative compounds, resulting in a first triazine derivative compound and a second triazine derivative compound that are the same or different from each other, wherein the luminescent region comprises (a) a hole transport zone comprising at least one of the anthracene derivative compound; (b) a light emitting zone comprising the first triazine derivative compound; and (c) an electron transport zone comprising the second triazine derivative compound.

14. The device of claim 1, wherein the luminescent region comprises (a) a hole transport zone comprising at least one of the anthracene derivative compounds; (b) a light emitting zone comprising at least one of the triazine derivative compounds; and (c) an electron transport zone.

15. The device of claim 1, wherein the luminescent region comprises (a) a hole transport zone comprising at least one of the anthracene derivative compounds; (b) a light emitting zone; and (c) an electron transport zone comprising at least one of the triazine derivative compounds.

16. The device of claim 1, wherein an anthracene derivative compound is

17. The device of claim 1, wherein the luminescent region includes two or more layers and each of the layers has a thickness ranging from about 50 Angstroms to about 2,000 Angstroms.

* * * * *